United States Patent
Howard et al.

(10) Patent No.: US 6,329,432 B2
(45) Date of Patent: *Dec. 11, 2001

(54) MESOZEAXANTHIN FORMULATIONS FOR TREATMENT OF RETINAL DISORDERS

(75) Inventors: Alan Norman Howard, Cambridge (GB); John T. Landrum; Richard A. Bone, both of Miami, FL (US)

(73) Assignee: The Howard Foundation, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/796,522

(22) Filed: Mar. 2, 2001

Related U.S. Application Data

(63) Continuation-in-part of application No. 08/774,052, filed on Dec. 23, 1996, now Pat. No. 6,218,436, which is a continuation-in-part of application No. 08/487,627, filed on Jun. 7, 1995, now abandoned, which is a continuation-in-part of application No. 08/266,768, filed on Jun. 28, 1994, now abandoned, which is a continuation-in-part of application No. 08/219,897, filed on Mar. 30, 1994, now abandoned.

(30) Foreign Application Priority Data

| Jun. 28, 1993 | (GB) | ................................................ 9313266 |
| Feb. 28, 1996 | (GB) | ................................................ 9604221 |
| Jun. 7, 1996 | (GB) | ................................................ 9611967 |

(51) Int. Cl.$^7$ ................................................ A61K 31/045
(52) U.S. Cl. ........................................ 514/725; 514/912
(58) Field of Search ................................ 514/725, 912

(56) References Cited

U.S. PATENT DOCUMENTS

| 4,048,203 | 9/1977 | Philip . |
| 5,290,605 | 3/1994 | Shapira . |
| 5,310,764 | 5/1994 | Baranowitz et al. . |
| 5,457,135 | 10/1995 | Baranowitz et al. . |

FOREIGN PATENT DOCUMENTS

| 4 020 874 | 1/1991 | (DE) . |
| 385 335 | 9/1990 | (EP) . |
| 672 655 | 1/1995 | (EP) . |
| 2 274 235 | 7/1994 | (GB) . |
| 2 280 110 | 1/1995 | (GB) . |
| WO 91/03571 | 3/1991 | (WO) . |
| WO 96/19215 | 6/1996 | (WO) . |

OTHER PUBLICATIONS

Mares–Perlman, et al., "Serum Antioxidants and Age–Related Mascular Degeneration in a Population–Based Case–Control Study," Archives of Opthalmology, Dec. 1995, vol. 113, pp. 1518–1523.

Seddon, et al., "Dietary Carotenoids, Vitamin A, C and E, and Advanced Age–Related Macular Degeneration," JAMA, Nov. 9, 1994, vol. 272, No. 18, pp. 1413–1420.

Snodderly, "Evidence for protection against age–related macular degeneration by carotenoids and antioxidants vitamins[1–3]," Am. J. Clin. Nutr., Dec. 1995, vol. 62, No. 6 (Supplementa), pp. 1448S–1461S.

"Schalch, W., Carotenoids in the retina—A review of their possible role in preventing or limiting damage caused by light and oxygen," Free Radicals and Aging (1992), pp. 280–298.

"Water–miscible carotenoid emulsions—contr. tris(hydroxymethyl) amino methane soaps as emulsifiers," Derwent World Pat., WPI Acc No.: 74–11689V/07.

Chemical Abstracts 1996:69194 (1995), Seddonerly.
Chemical Abstracts 12:79918 (1994) Seddon et al.

.Rousseau, E.J.N., "Carotenoids and Other Dietary Antioxidants in Free Radical Research: Protection of Human Retina Homogenate Against Photochemical and Metal–Induced Lipid Autoxidation," Dissertation Abstracts Online, vol. 34/02 of Masters Abstracts, p. 733 (1994).

Alpha tocopherol bitamin =An acid ester contg. oil compsn.—contg. carotenoids(s), used as cosmetic to inhibit skin deterioration and as anticulcer agent,: Derwent WPI, WPI Acc No.: 93–239918/30.

"Singlet–oxygen–removing compsn.—contains, e.g., alpha or beta carotene and antioxidant, used for controlling peroxidation of lipid on skin," Derwent WPI, WPI Acc. No.: 94–012180/02.

"Pharmaceutical compsn. contg. heron egg yolk—for restoring balance between iron and gold in the blood," Derwent World Pat., WPI Acc No.: 80–90343C/51.

"The Effect of a Dietary Lack of Xanthophyll on the Eye of the Monkey," Nutr. Rev., Nov. 1980, vol. 38, No. 11, pp. 384–386.

Seddon et al., "Do antioxidants prevent or retard the onset of AMD?", J. Am. Osteopath. Assoc., Jan. 1995, vol. 95, No. 1, p. 26.

J.T. Landrum et al., "Macular Pigment Steromens in Individual Eyes: A Comparison Between Normals and Those with Age–Related Macular," Investigative Opththalmology * Visual Science, Mar. 15, 1995, vol. 36, No. 4, Abstr. No. 4094–75, p. S892.

"Buccal compsn., for preventing tooth decay and periodontal disease—contains xanthophyll(s) and/or carotene(s) contg. alpha–carotene," Derwent WPI, WPI Acc No. 94–115117/14.

"Fat emulsion for injection, comprising carotenoid—used for intravenous supply of nutrition after operation," Derwent WPI, WPI Acc No.: 94–221775/27.

*Primary Examiner*—Zohreh Fay
(74) *Attorney, Agent, or Firm*—Pillsbury Winthrop LLP

(57) ABSTRACT

Meso-zeaxanthin compositions for pharmaceutical use and use of meso-zeaxanthin to increase the deposition of macular pigment in the human eye, and for the therapeutic treatment or prophylaxis of diseases and disorders of the macula, in particular age-related macular degeneration (AMD).

11 Claims, 13 Drawing Sheets

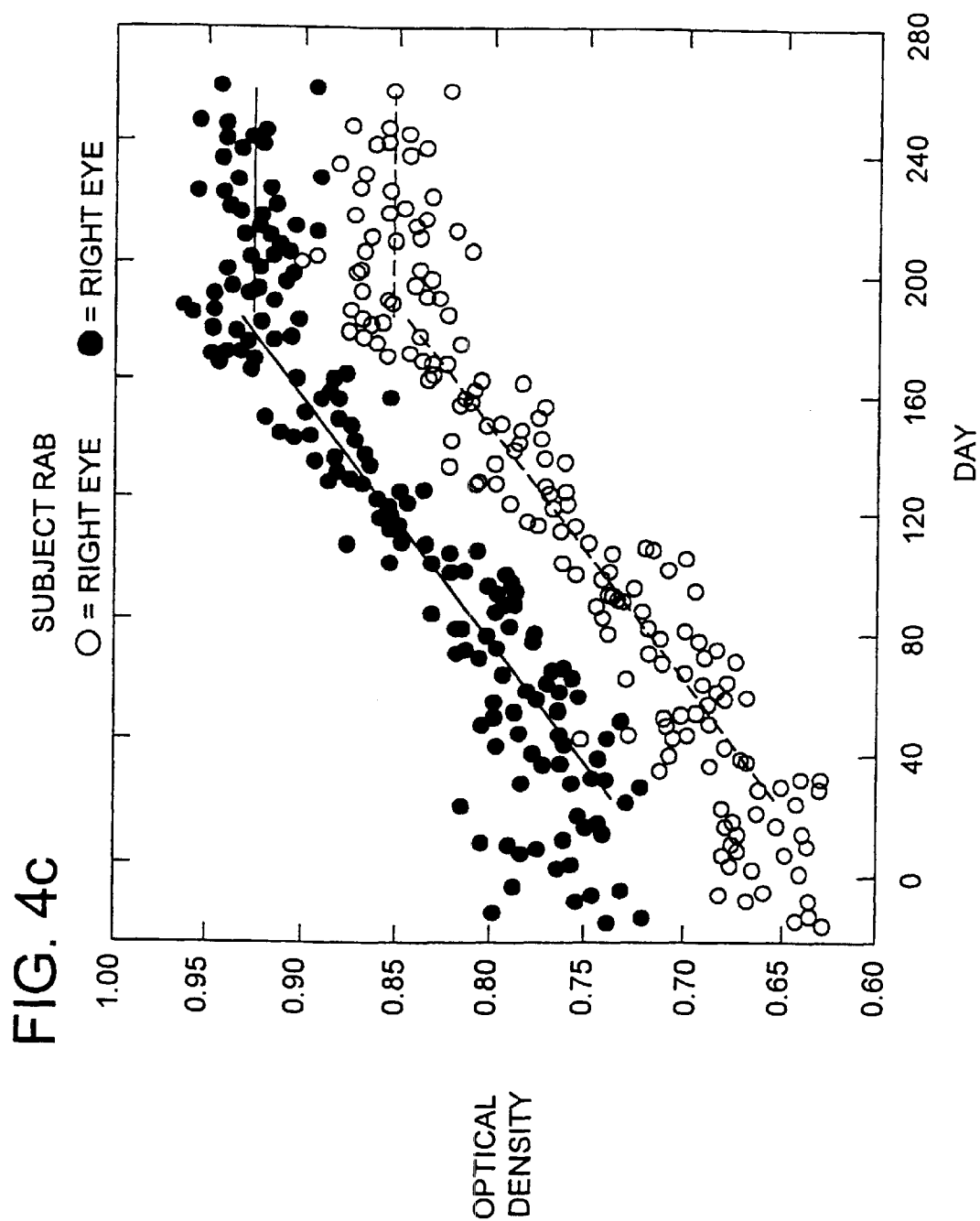

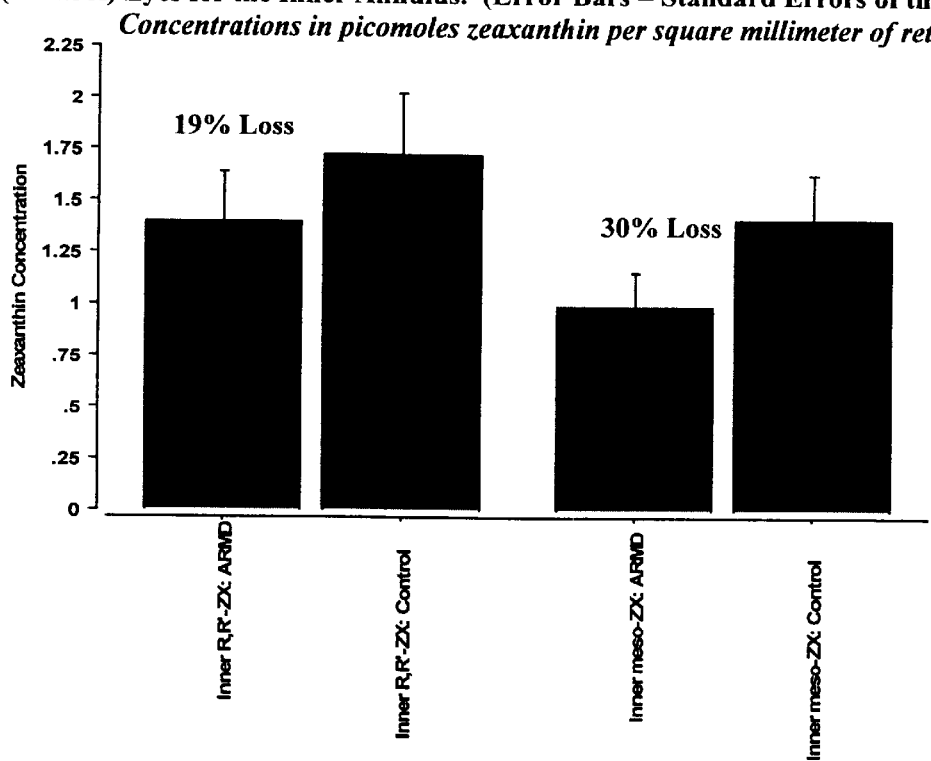
Figure 6: Bar Graphs Representing Zeaxanthin Concentrations in AMD and non-AMD (Control) Eyes for the Inner Annulus. (Error Bars = Standard Errors of the Mean). Concentrations in picomoles zeaxanthin per square millimeter of retina

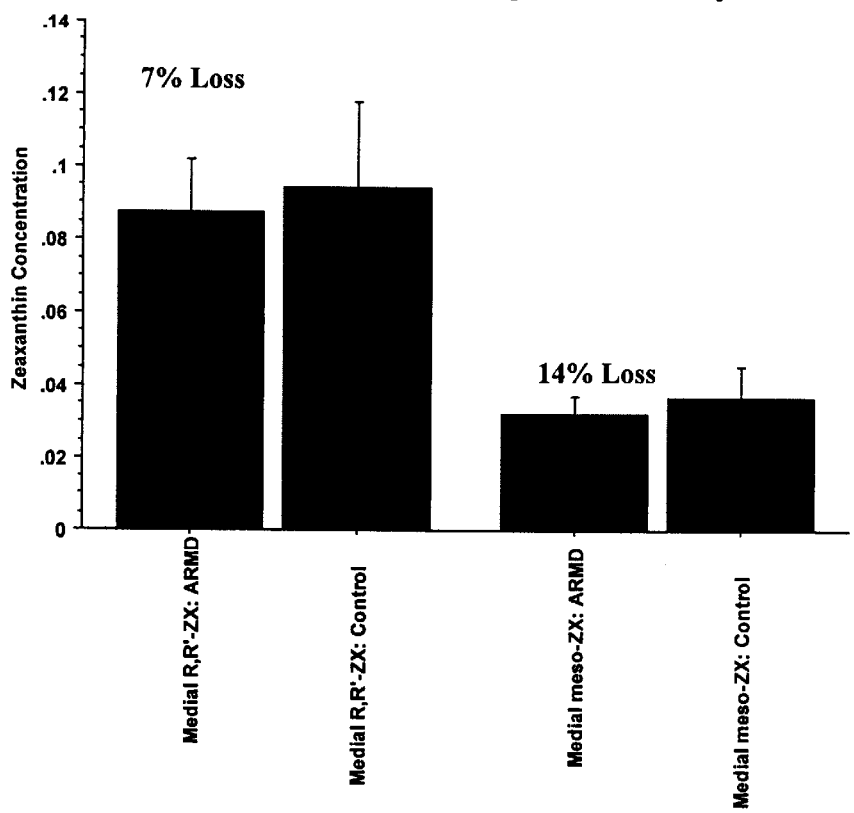
Figure 7: Bar Graphs Representing Zeaxanthin Concentrations in AMD and non-AMD (Control) Eyes for the Medial Annulus. (Error Bars = Standard Errors of the Mean).
*Concentrations in picomoles zeaxanthin per square millimeter of retina*

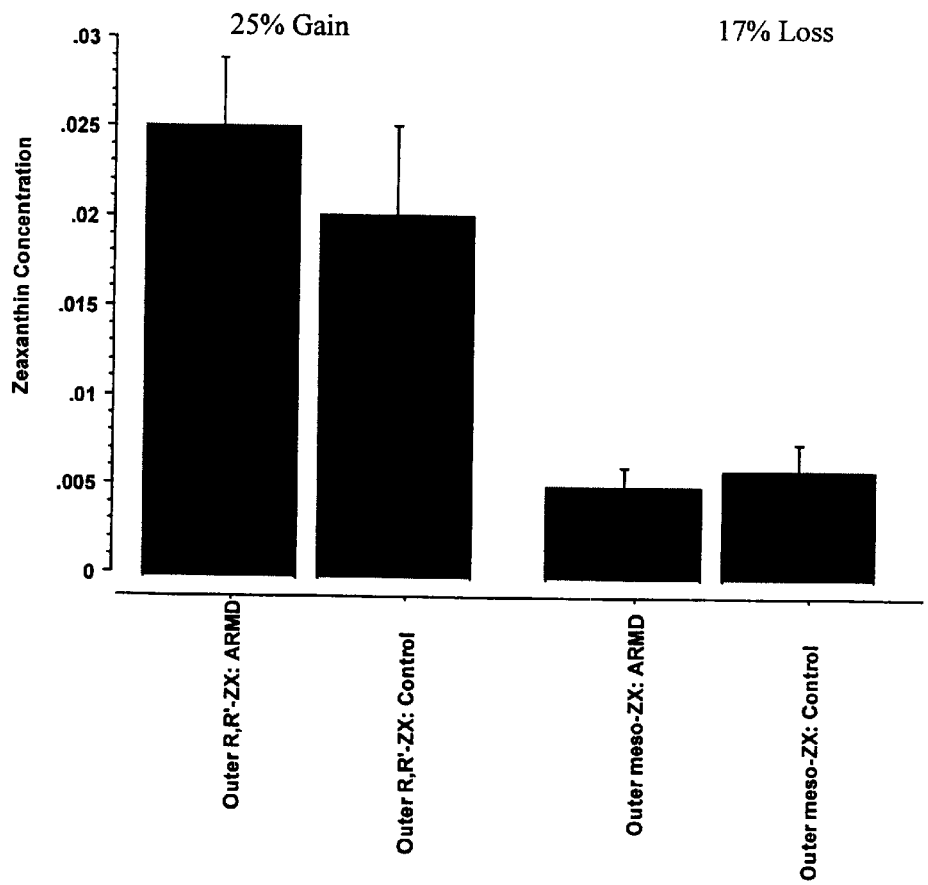
Figure 8: Bar Graphs Representing Zeaxanthin Concentrations in AMD and non-AMD (Control) Eyes for the Outer Annulus. (Error Bars = Standard Errors of the Mean).
*Concentrations in picomoles zeaxanthin per square millimeter of retina*

MESOZEAXANTHIN FORMULATIONS FOR TREATMENT OF RETINAL DISORDERS

This application is a continuation-in-part of U.S. application Ser. No. 08/774,052, filed Dec. 23, 1996 now U.S. Pat. No. 6,218,436, which is a continuation-in-part of U.S. application Ser. No. 08/487,627, filed Jun. 7, 1995 now abandoned, which is a continuation-in-part of U.S. application Ser. No. 08/266,768, filed Jun. 28, 1994 now abandoned, which is a continuation-in-part of U.S. application Ser. No. 08/219,897, filed Mar. 30, 1994 now abandoned, which claims the priority of application no. 9313266.0 filed in Great Britain on Jun. 28, 1993, the subject matter of each of which is incorporated herein by reference.

BACKGROUND OF THE INVENTION

1. Field of the Invention

The invention relates to the use of meso-zeaxanthin to increase the deposition of macular pigment in the human eye, and for the therapeutic treatment or prophylaxis of diseases and disorders of the macula, and in particular age-related macular degeneration (AMD).

2. Background Information

The macula is the anatomical region of the retina which in man is responsible for central vision. Centered on the fovea, where the visual axis meets the retina, it extends radially outwards to a distance of about 2.75 mm (Davson, 1990). The macula is divided into the inner macula and the outer macula. The inner macula extends radially out to a distance of 1.5 mm while the outer macula is defined by the surrounding annular ring. The central portion of the macula is easily recognizable because of its yellow coloration which results from the presence of macular pigment.

Despite its small size, the macula is endowed with the highest degree of visual acuity. It is therefore not surprising that considerable effort is devoted to understanding and, when possible, treating diseases which disrupt the nominal functioning of the macula. One such disease is age-related macular degeneration (AMD) which occurs in about 20% of the population above the age of 65 and is the leading cause of visual impairment in the USA and UK. AMD has up to the present time been an irreversible condition.

Pooled extracts of the macular pigment were found by Wald (1945) to have a carotenoid-like absorption spectrum which appeared to match that of lutein. Further work in the 1980's demonstrated that it consisted of lutein and zeaxanthin (Bone et al., 1985).

More recent work (Bone et al., 1993) has shown that the zeaxanthin component found in the human retina is itself composed of all three of the possible stereoisomers. FIG. 1 shows the stereochemical structures of the macular pigment components. The 3' hydroxy groups on lutein and meso-zeaxanthin have the same absolute configuration making interconversion possible by a movement of the 4', 5' double bond (lutein) to the 5', 6' position (meso-zeaxanthin). Of the three stereoisomers, SSZ is present only as a relatively small component. RRZ is of dietary origin whereas RSZ (meso-zeaxanthin) is not common in the diet and is not detected in human serum. It has been suggested that the presence of RSZ may be the result of isomerization of lutein to RSZ by an enzyme.

The function of the macular pigment has not been unequivocally determined. It has been proposed that one function may be to reduce the adverse effect of chromatic aberration in the ocular media thereby increasing acuity (Walls, 1967, Reading and Weale, 1974). A more generally held current view is that the pigment probably acts in a protective capacity against the damaging effects of blue light (Dicthburn, 1973; Kirshfeld, 1982; Bone et al., 1984) which can induce the formation of reactive free radicals within the retina and the formation of such species may be greatly reduced in individuals having a high level of macular pigmentation. The macular pigment may also serve passively as a filter and shield sensitive tissues from harmful excessive blue light.

AMD is a disease that develops gradually over a period of many years with loss of sight being the ultimate result. The damaged tissue has an unusually high lipid content that it has been suggested oxidizes to form lipofuscin, a fluorescent product of lipid oxidation. It has been postulated that exposure of the retina to excessive blue light may increase the rate of lipofuscin formation (Feeney-Burns et al., 1990; Gottsch et al., 1990).

To date, little is known about the factors that influence the uptake of carotenoids into the macula and there is no effective cure or prevention of AMD.

The studies of plasma carotenoids in case control studies of AMD have been equivocal. In the Beaver Dam eye study (Mares-Perlman et al., 1995), no differences were observed between 167 cases and 167 controls in serum including lutein or zeaxanthin. In the Eye Disease Case Control Study Group (1993) results of 421 cases and 615 controls were reported. People with serum carotenoid levels in the medium to high group had one half to one third risk of AMD compared with the low group. All of the carotenoids measured, including lutein, zeaxanthin, beta carotene, alpha carotene and cryptoxanthin were implicated. In a further publication (Seddon et al., 1994), these authors found that the consumption of lutein and zeaxanthin (which are primarily obtained from dark green leafy vegetables) were most strongly associated with a reduced risk of AMD. However, some people with a high consumption of green vegetables still suffered from AMD.

In an abstract published in the March 1995 issue of Investigative Ophthalmology and Visual Science (36, suppl, 892), the carotenoid analysis of 8 normal eyes and 8 eyes from patients with AMD was reported. The results suggested a positive correlation existed between lowered macular pigment and the prevalence of AMD, but recommended that caution should be exercised in this interpretation because the reduced macular pigment could be a result, rather than a cause of the disease. When the subject matter of the above mentioned abstract was submitted for publication to a peer-reviewed journal, the referees recommended rejection because the number of samples analyzed was too small. Further results were therefore necessary before any conclusion could be made on the possible preventative role of lutein/zeaxanthin in AMD.

SUMMARY OF THE INVENTION

It is the object of the present invention to increase macular pigment and to prevent or cure AMD by the administration of in meso-zeaxanthin.

It is a further object of the invention to provide novel compositions comprising meso-zeaxanthin either alone or in combination with other pharmaceutically effective compounds for the treatment and/or prevention of AMD.

Within the above context, we anticipate that supplements containing meso-zeaxanthin or an ester thereof will increase the macular pigment in the human macula which is expected to lead to the prevention and/or treatment of AMD in those people at risk of or having the disease.

It has been found in a sufficiently large sample to warrant conclusions, that the lutein/zeaxanthin content of the retinas of eyes from people with AMD was 30% less than in normal eyes. While it could be expected that since the macula contains lutein/zeaxanthin, the administration of lutein/ zeaxanthin in quantities similar to that occurring in green vegetables would raise the cocentration of macular pigment, it has been found rather surprisingly that when certain carotenoids, such as lutein, are given orally in concentrated form the amount required to be effective in the short term is considerably greater than expected.

Meso-zeaxanthin not being found in normally consumed foodstuffs, the concentration to be administered for effective treatment is greater than that which is found in the normal human diet. Accordingly, the present invention in one aspect provides meso-zeaxanthin for the use as pharmaceutical or food supplements, particularly in the elevation of macular pigment and the prevention or management of age related macular degeneration. For this purpose, meso-zeaxanthin may be administered alone, or with pharmaceutically acceptable excipients or carriers, or in combination with other active compounds such as lutein and other carotenoids.

Generally speaking, the meso-zeaxanthin may be used in the total dosage regime of up to 100 mg per day, typically 0.5–50 mg/day with an optimum dosage of 5–10 mg/day. The dosage depends upon the time of administration. When the macula is depleted of macular pigment, a relatively high dose of lutein (circa 30 mg/day) is normally used.

During the initial period of administration, it is preferred to use a large dose of meso-zeaxanthin, circa 30 mg/day. However, when a plateau is achieved in the concentration of macular pigment, a maintenance dose of, for example, 5–10 mg/day, or lower, may be sufficient. One reason for reducing the dosage is that at the high dose, the skin may turn yellow due to the yellow color of the compound. Whilst this undesirable side effect can be tolerated for a short time, a lower dose is preferable for maintenance because it does not cause skin pigmentation.

A unit dosage form such as, for example, a 750 or 800 mg tablet to be used on a one-a-day basis may contain from 0.1% to about 12.5% by weight of meso-zeaxanthin and other ingredients including the following

| | |
|---|---|
| Beta carotene | about 2 to about 20 mg (preferably about 5 mg) |
| Lycopene | about 2 to about 20 mg (preferably about 5 mg) |
| Vitamin A | about 400 to about 600 RE (preferably about 500 RE) |
| Vitamin C | about 75 to about 250 mg (preferably 100 mg) |
| Vitamin E | about 50 to about 250 mg (preferably about 100 mg) |
| Selenium | about 80 to about 120 mcg (preferably about 90 mcg) |
| Copper | about 2 to about 4 mg (preferably about 3 mg) |
| Zinc | about 10 to about 20 mg (preferably about 15 mg) |
| Manganese | about 2 to about 5 mg (preferably about 4 mg) |
| Ubiquinone (Coenzyme Q10) | about 10 to about 100 mg (preferably about 50 mg) |
| Carrier | about 150 to about 250 mg (preferably 175–200 mg) |

Accordingly, one aspect of the invention consists of a high dose of meso-zeaxanthin followed by a lower dose when the macular pigment reaches a plateau. For those skilled in the art, macular pigmentation can be measured by a flicker photometer (see Example 2).

As will be seen from FIG. 1 of the drawings, lutein and the three forms of zeaxanthin are isomers. The three forms of zeaxanthin are zeaxanthin (the 3R, 3'R form) meso-zeaxanthin (the 3R, 3'S form) and 3S, 3'S zeaxanthin.

Meso-zeaxanthin can be used alone or in combination with the other isomers, in free form or in the form of an ester. Typically such esters are $C_1$ to $C_{18}$ esters, for example ethyl esters, or esters with long chain fatty acids, for example lauric, myristic or palmitic esters. In another aspect, the invention provides a food supplement or pharmaceutical composition comprising meso-zeaxanthin or an ester thereof together with a food supplement or pharmaceutically accepted diluent or carrier.

Such a composition may be in bulk form, or more preferably, unit dosage form. Thus, for example, the composition may be formulated as a tablet, capsule, powder, solution or suspension.

Compositions in accordance with the invention may be prepared using meso-zeaxanthin or ester active agent in accordance with conventional fool supplement or pharmaceutical practice. The diluents, excipients or carriers that may be used are well known in the formulation art and the form chosen for any particular regimen will depend on the given context and the formulator's choice.

The invention includes within its scope meso-zeaxanthin for use as a pharmaceutical. It is thought that when administering meso-zeaxanthin in combination with other substances, as mentioned above, the patient will benefit through a synergism between meso-zeaxanthin and other active agents, particularly other carotenoid compounds. Amongst other agents there may be mentioned, for example lycopene or alpha, beta, gamma or delta carotene, or one or more of the following antioxidants, namely vitamin A, vitamin C, vitamin E (alpha-tocopherol and other active tocopherols), selenium, copper, zinc, manganese and Ubiquinone (coenzyme Q10). Use of a mixture containing a tocopherol such as α-tocopherol is especially preferred since it is believed that such a mixture affords a synergistic effect.

The carotenoids are partially destroyed in the gastrointestinal tract by oxidation. By adding vitamin E and/or vitamin C, this process is inhibited and more carotenoid is absorbed. The inhibitor may be included as part of a composition, or administered separately. In addition to the above aspects, the invention includes the use of meso-zeaxanthin and esters thereof, for increasing the pigment in the macula of the human eye for treatment or prevention of age related macular degeneration or other macular pigment depreciation maladies.

The compositions of the invention may be administered in tablets or capsule form, or in liquid form, or other suitable forms familiar to those of skill in the art. The preferred route of administration is oral.

The formulations may conveniently be prepared in unit dosage form by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

In one embodiment, the composition takes the form of capsules, each capsule containing an effective dosage of a meso-zeaxanthin composition, with a suggested dosage of one to four capsules per day.

Furthermore, the invention includes a process for the manufacture of a food supplement or medicament for the above-mentioned purposes. This process comprises combining meso-zeaxanthin in suitable amounts with one or more pharmaceutical acceptable carriers and/or diluents to produce a food supplement or medicament that will be effective for the prevention and/or treatment of AMD. The process may also include the addition of other active compounds as noted hereinbelow.

BRIEF DESCRIPTION OF THE DRAWINGS

FIG. 4c shows daily macular pigment optical density measurements for the same subject as is the case in FIG. 4b for a longer period of lutein administration which includes the period represented in FIG. 4b.

FIG. 6 shows bar graphs representing zeaxanthin concentrations in AMD and non-AMD (control) eyes for the inner annulus. (Error bars=standard errors of the mean).

FIG. 7 shows bar graphs representing zeaxanthin concentrations in AMD and non-AMD (control) eyes for the medial annulus. (Error bars=standard errors of the mean).

FIG. 8 shows bar graphs representing zeaxanthin concentrations in AMD and non-AMD (control) eyes for the outer annulus. (Error bars=standard errors of the mean).

DETAILED DESCRIPTION OF THE INVENTION

The following examples are intended to illustrate the invention by way of example only, and are not intended to limit the scope of the invention.

EXAMPLE 1

1.1 Analysis of carotenoids in eyes

An HPLC analysis of retinas obtained from normal and AMD individuals was conducted using a sufficiently large sample to warrant conclusions on the importance of macular lutein and zeaxanthin in the prevention of AMD. The amount and distribution of the macular carotenoids, including the stereoisomers. were determined and compared for 15 normal and 22 AMD eyes in order to determine if there is evidence for or against the hypothesis that macular pigment protection from light exposure plays a significant role in reducing AMD.

For each normal and AMD eye, the neural retina was cut into a central disk and 2 concentric annuli using trephines of 3, 11 and 21 mm. to extract the carotenoids, the tissues were ground in ethanol/water (1:1) to which 10 ng lutein monomethyl ester was added as an internal standard. Separation and quantitation of zeaxanthin and lutein fractions was by reversed-phase HPLC using Phenomenex column.

Figure 1:
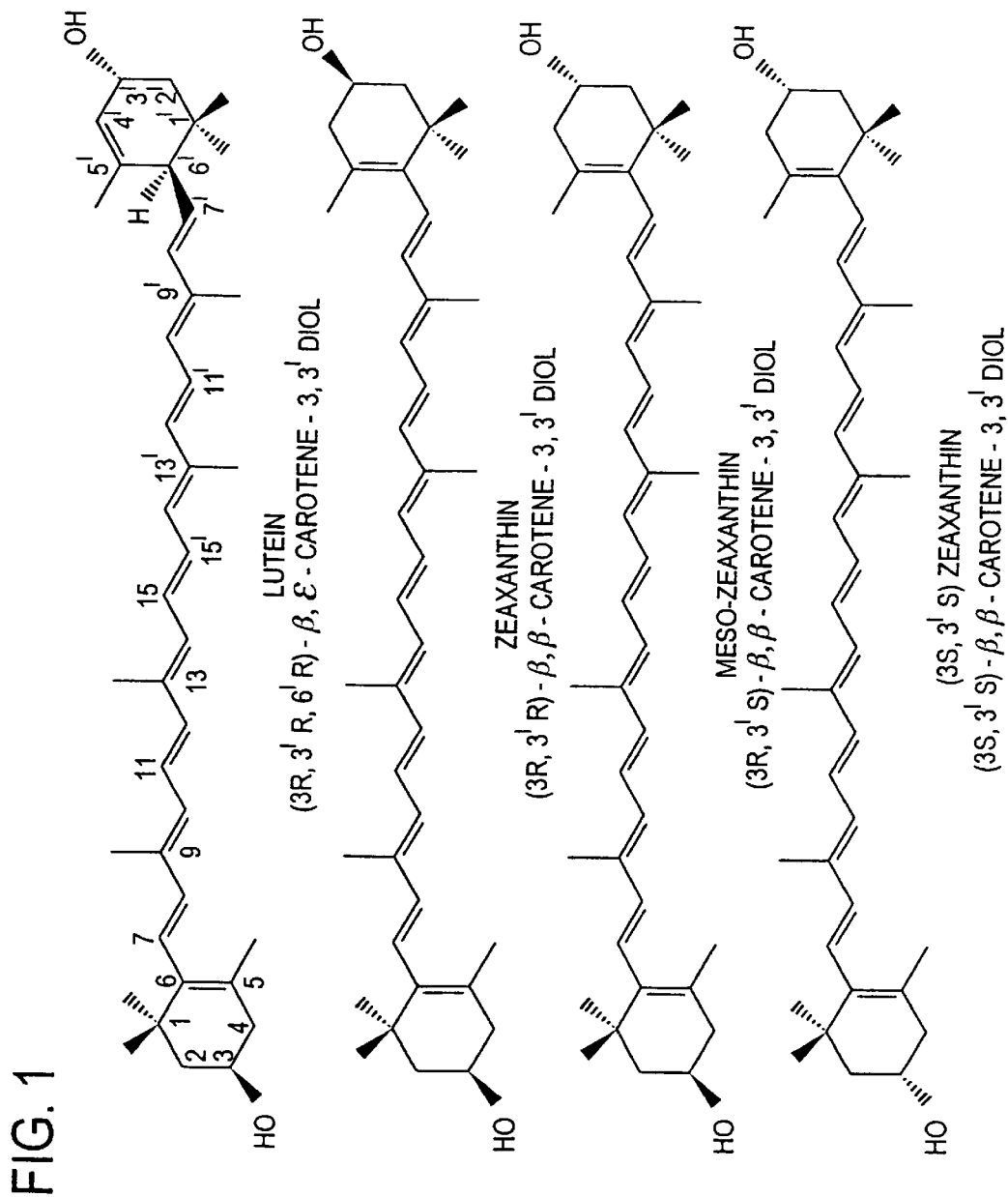
FIG. 1 shows the structures of lutein, 3R,3'R-, 3R,3'S- and 3S,3'S- zeaxanthin.
Figure 2:
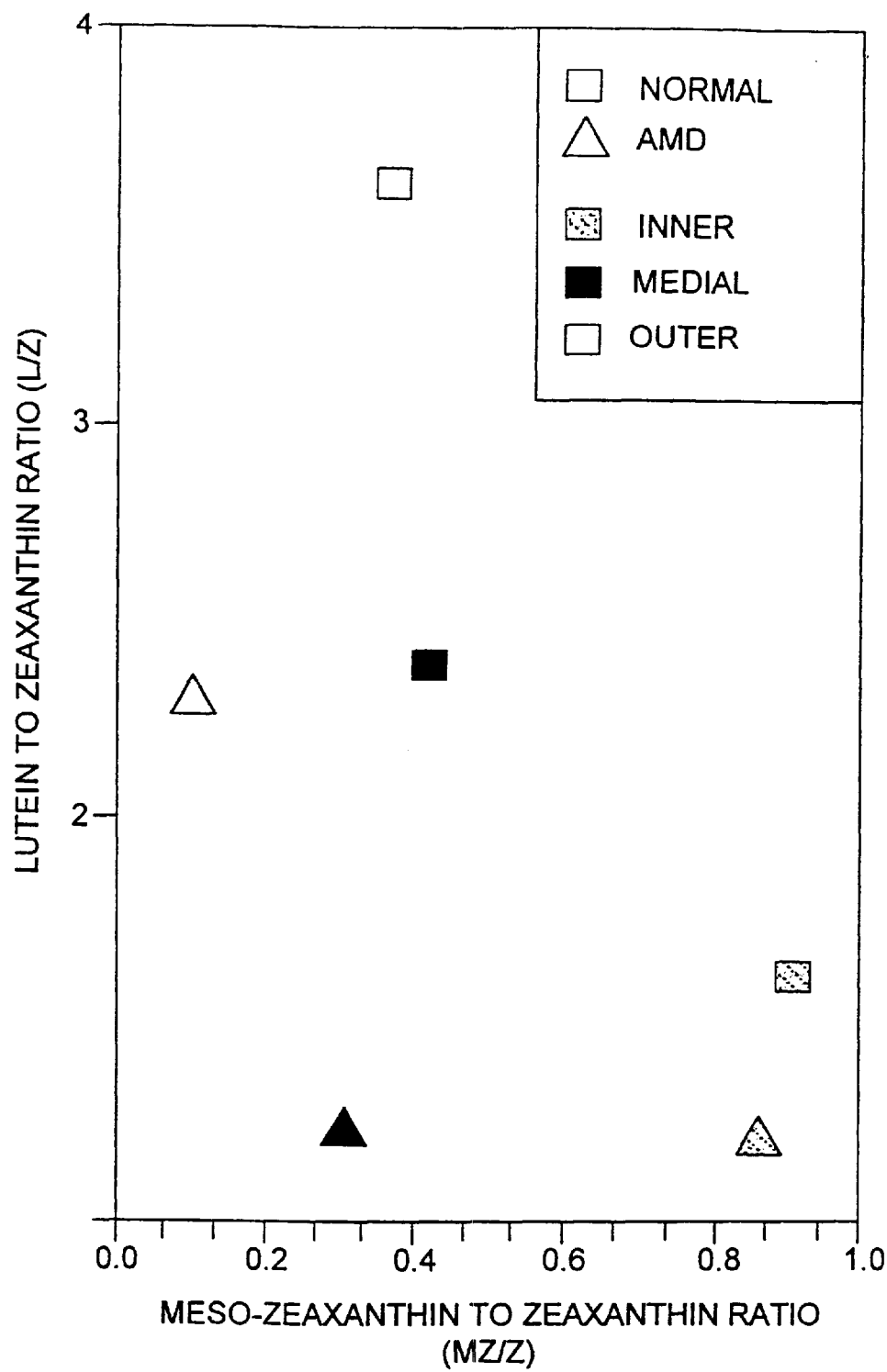
FIG. 2 shows for both normal and AMD eyes the average L:Z ratio for each disc or annulus of retinal tissue plotted against the average MZ:Z ratio. The ratios of lutein to zeaxanthin and meso-zeaxanthin are consistently lower for AMD eyes as compared to normals.

Carbamate derivatives of individual stereoisomers of both zeaxanthin and lutein were separated on a normal-phase HPLC column, using the methods of Ruttiman et al (1983) and Schiedt et al. (1995), the results being plotted in FIG. 2.

1.2 Results and Conclusions

As shown in Table 1, AMD eyes had on average approximately 70% of the total carotenoid found in controls, a figure that was very consistent across the retina. Seventeen (77% of the twenty two AMD eyes had total amounts of lutein and zeaxanthin in the central 3 mm of the retina which were below the mean 5.9 pmole/mm2) for the control group. For the two annuli, having outer diameters of 11 and 21 mm respectively, 15 (68%) of the AMD group were found to be lower in total carotenoids than the corresponding regions in the control group.

The differences observed between the control and AMD eyes in the inner annuli were found to be statistically significant (on a one sided test $p<0.05$); the difference in the medial and outer annuli were found almost significant ($p<0.1$).

The relative distributions of carotenoids throughout the retina for normal and AMD eyes were found to be essentially the same, both groups were characterized by a decrease in the quantity of meso-zeaxanthin and a relative increase in lutein with increasing distance from the fovea. The relative amounts of lutein and meso-zeaxanthin as compared to zeaxanthin are consistently lower in the AMD retinas as compared to normal retinas.

TABLE 1

Total carotenoid/unit area in retinas from control subjects and those with AMD
TOTAL CAROTENOID/UNIT AREA pmoles/mm²

| [1]Donor # | INNER (7.1 mm²) | MEDIAL (93 mm²) | OUTER (343 mm²) |
|---|---|---|---|
| CONTROL EYES | | | |
| 1 | 12.8 | 0.88 | 0.19 |
| 2 | 10.5 | 0.51 | 0.10 |
| 3 | 10.4 | 0.89 | 0.18 |
| 4 | 9.3 | 1.35 | 0.36 |
| 5 | 8.4 | 0.38 | 0.07 |
| 6 | 5.8 | 0.19 | 0.06 |
| 7 | 5.3 | 0.23 | 0.43 |
| 8 | 5.1 | 0.48 | 0.21 |
| 6 | 4.7 | 0.15 | 0.05 |
| 9 | 4.6 | 0.21 | 0.06 |
| 9 | 4.3 | 0.18 | 0.05 |
| 10 | 2.5 | 0.07 | 0.03 |
| 10 | 2.2 | 0.08 | 0.03 |
| 11 | 2.0 | 0.26 | 0.20 |
| 12 | 1.0 | 0.09 | 0.02 |
| Control average ± sd | 5.9 ± 3.4 | 0.4 ± 0.36 | 0.14 ± 0.12 |

TABLE 1-continued

Total carotenoid/unit area in retinas from control
subjects and those with AMD

TOTAL CAROTENOID/UNIT AREA pmoles/mm$^2$

| [1]Donor # | INNER (7.1 mm$^2$) | MEDIAL (93 mm$^2$) | OUTER (343 mm$^2$) |
|---|---|---|---|
| AMID EYES | | | |
| 13 | 9.5 | 0.47 | 0.19 |
| 13 | 9.4 | 0.78 | 0.23 |
| 14 | 8.4 | 0.30 | 0.12 |
| 14 | 7.7 | 0.56 | 0.13 |
| 15 | 6.7 | 0.17 | 0.09 |
| 16 | 5.7 | 0.24 | 0.08 |
| 17 | 4.8 | 0.47 | 0.15 |
| 18 | 4.5 | 0.34 | 0.07 |
| 16 | 4.5 | 0.20 | 0.06 |
| 19 | 4.5 | 0.14 | 0.05 |
| 17 | 4.0 | 0.24 | 0.11 |
| 19 | 3.8 | 0.05 | 0.09 |
| 20 | 3.4 | 0.45 | 0.16 |
| 21 | 3.4 | 0.20 | 0.09 |
| 20 | 2.4 | 0.46 | 0.13 |
| 22 | 2.3 | 0.13 | 0.05 |
| 22 | 1.9 | 0.11 | 0.06 |
| 23 | 1.2 | 0.03 | 0.02 |
| 1 | 0.71 | 0.47 | 0.19 |
| 23 | 0.46 | 0.03 | 0.02 |
| 24 | 0.43 | 0.10 | 0.03 |
| 24 | 0.32 | 0.07 | 0.02 |
| AMD average±sd | 4.1 ± 2.8 | 0.27 ± 0.20 | 0.097 ± 0.058 |

[1]For cases where there are two estimations from the same donor, the first is from the left eye and the second is from the right eye.

EXAMPLE 2

Uptake of Lutein in Human Adults 2.1 Serum Uptake

A trial was conducted to determine if dietary supplementation with lutein and zeaxanthin effectively can change the pigment levels in the macula. The optical density of the macula pigment was measured for each subject using the method of flicker photometry (Bone and Sparrock 1971; Bone et al 1992). The concentration of pigment in the macula is proportioned to its optical density and the actual amount of pigment was assumed to be proportional to concentration. Thus, optical density was taken as a measure of the total amount of pigment.

Serum lutein and zeaxanthin was measured by conventional HPLC.

Two healthy adult males (of age/weight 42 year/60 kg and 51 years/61 kg) ingested the equivalent of 30 mg of lutein per day in the form of lutein esters (source: marigold flowers) suspended in 2 ml of canola oil. This was continued over a period of 138 days and then the dose of lutein was discontinued. Chemical analysis has shown that the product contains approximately $^{97}$% lutein -and 3% zeaxanthin. Fasting serum lutein/zeaxanthin levels of both individuals were determined by conventional HPLC on the morning of the first dose as a measure of base line. Blood samples were drawn at 2–3 hour intervals throughout the first day for both subjects and then daily for the next three days. Following the first week of supplementation, blood samples were drawn weekly. Blood was collected into a standard Vacutainer serum separator tube containing no anticoagulant. After allowing about 30 min for coagulation, the sample was centrifuged for 10 minutes and the serum removed by pipette. Serum samples were stored at −20° C. prior to analysis. Carotenoids ware extracted from the serum by a minor modification of widely used methods (Guiliano et al, 1993; Handelmann et al, 1992), 200 μl aliquots of serum were diluted with 2 mL of 50% ethanol/water to ensure precipitation of protein components. 20 μl of an internal standard, monohexyl lutein ether, containing about 90 ng, was added to the solution at this point for quantification of the carotenoids by HPLC. This solution was extracted 3 times with 2 mL portions of hexane by vortexing the sample for 1 min followed by centrifuging for 5 minutes and pipetting off the hexane layer. The three portions of hexane were dried under a stream of nitrogen gas and stared under nitrogen at −20° C. until analysis was completed.

Serum extracts were dissolved in 4.0 μL of ethanol prior to injection. Samples were vigorously agitated on a vortex mixer for 1 min to ensure dissolution of the sample. Two replicate analyses were carried out using 20 μL aliquots. Serum carotenoids were eluted at a flow rate of 1 mL/min through a 15 cm×4.6 mm. Adsorbosphere ODS 3 μm HS column (Alltech) coupled to a 25 cm×4.6 mm Spherisorb ODS 5 μm column (Keystone Scientific) with detection of the carotenoids at 451 nm.

Figure 3A:
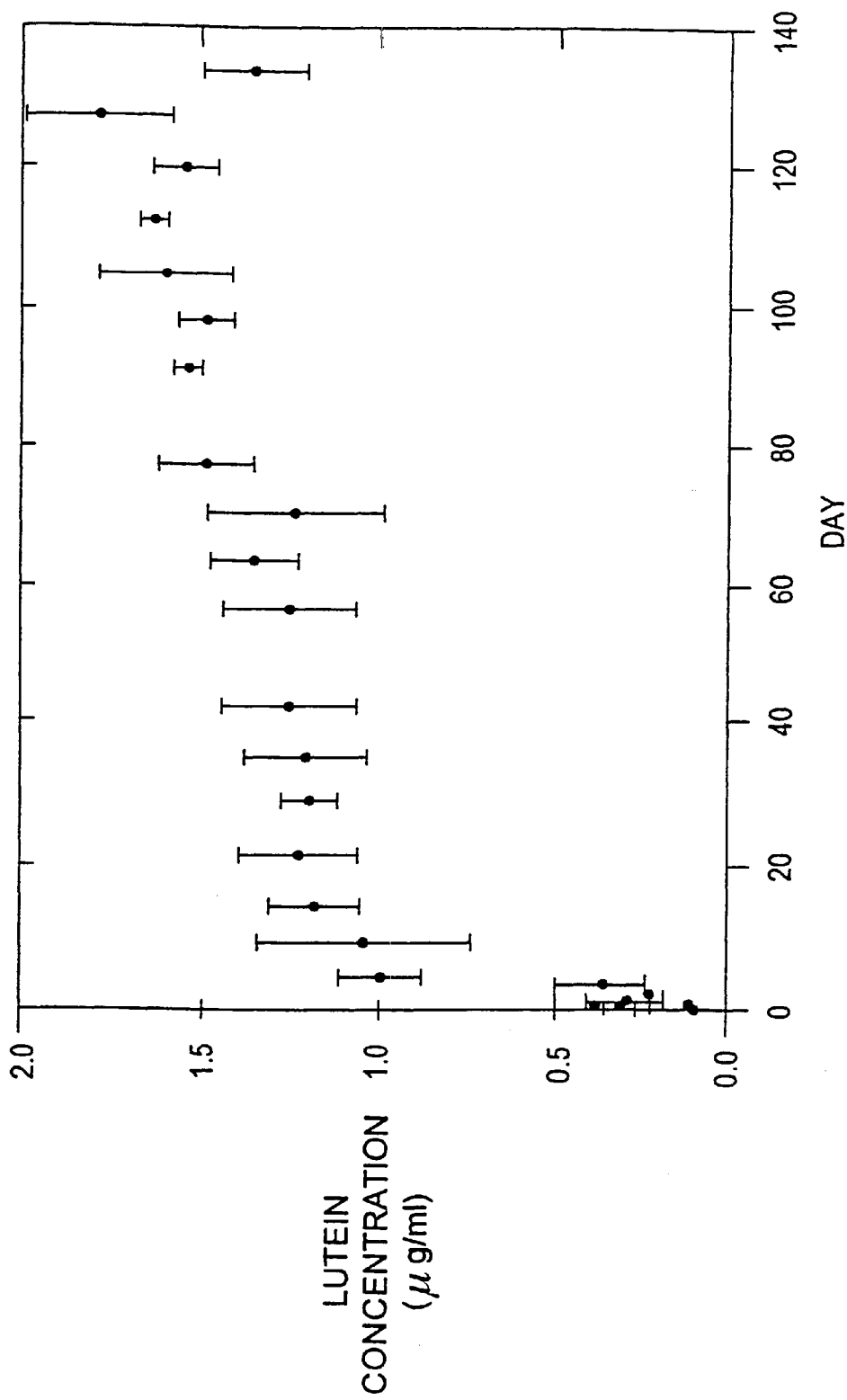
FIG. 3a shows the time-dependent increase in the serum lutein level of Subject JTL (Example 2). Error bars represent the standard deviations in the measurements. Day "0" represents the beginning of lutein supplementation.
Figure 3B:
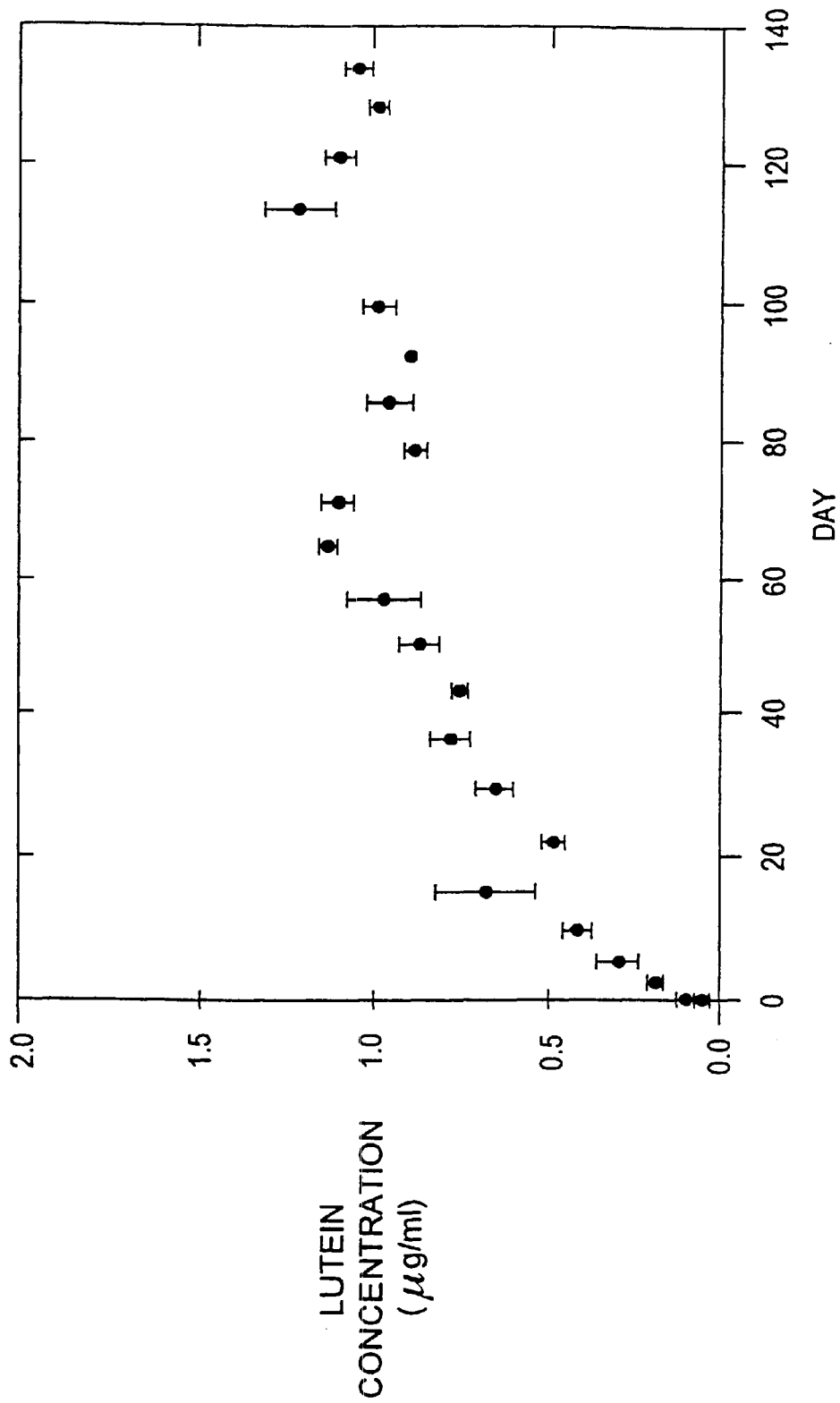
FIG. 3b shows the time dependent increase in the serum lutein level of subject RAB (Example 2). Error bars represent the standard deviations in the measurements. Day "0" represents the beginning of lutein supplementation.

FIGS. 3a and 3b show the increase in serum lutein concentration in the two subjects during the time course of the supplementation experiment. The concentration of lutein in both subjects increased by a factor of about 10 times within the first week and remained high thereafter.

Two other subjects LLM and KEG each receiving 30 mg/day lutein ester also showed large increases in serum lutein concentrations.

Subject LLM increased from 0.5 μg/m to 1.20 μg/ml in 50 days and then reached a plateau. Subject KES increased from 0.20 μg/ml to 1.22 μg/ml in 50 days.

2.2 Macular Uptake

The optical density of the macular pigment was measured for each subject using the method of heterochomatic flicker photometry (Bone and Sparrock, 1971; Bone et al, 1992). The concentration of pigment in the macula is proportional to its optical density and the actual amount of pigment was assumed to be proportional to concentration. Thus optical density was taken to be a measure of the total amount of pigment.

In the flicker method, a small visual stimulus is presented to the eye which alternates in wavelength between 460 nm, the peak absorbance wavelength of the macular pigment, and 540 nm where pigment absorbance is zero (Bone et al., 1992). Above a certain frequency, color fusion occurs but the stimulus continues to flicker. At a higher frequency, a critical condition can be reached where flicker can be eliminated only if the two wavelength components are matched in luminance. If the stimulus is viewed peripherally, so that the image falls outside the macula, neither wavelength is attenuated by the macular pigment. However, if the stimulus is viewed centrally, the intensity of the 460 nm light must be increased to compensate for absorption by the macular pigment in order to achieve a luminance match. Thus it is possible to determine the optical density of a subject's macular pigment at the peak wavelength, or indeed any other wavelength.

The validity of this technique depends on the relative spectral response of the receptors being the same in the central and peripheral locations used. The flicker, which the subject seeks to eliminate, is one of luminance and, assuming phototopic conditions, luminance is most likely due to an additive response from the long and middle wavelength sensitive cones (Guth et al, 1980).

There is evidence that these two cone types are present in equal ratios in the two locations used (Wooten and Wald, 1973). The short wavelength cones, whose relative abundances differ between the two locations, are generally not assumed to contribute to luminance (Guth et al, 1980), though others, using flicker techniques, have sought to eliminate their participation (Pease at al, 1987; Werner et al.

1987; Hammond et al 1995). The ultimate justification for our procedure is to be found in the accurate reproduction of the macular pigment absorbance spectrum which it generates (Bone et al, 1992).

The apparatus consisted of a two-channel Maxwellian view system based on a single light source, a 75 W xenon arc lamp. The wavelengths of the two channels were determined by 460 nm and 540 nm interference filters respectively, having half-widths of 7 and 9 nm. The channels were combined by a rotating semicircular mirror, and a circular aperture in a white screen provided a 1.5° diameter stimulus. Cross-hairs facilitated central fixation of the stimulus. The screen was 18° in diameter and was illuminated with white light from the same source. The illuminance of the screen was adjusted to provide the same retinal illuminance of 4 log Td as the stimulus. This was considered to be sufficiently high to minimize proteins associated with rod intrusion which could otherwise differentially affect measurements in the macula and peripheral retina (Wyszcki and Stiles, 1982). A small red LED was located 8° above the centre of the stimulus to provide a fixation mark for peripheral viewing of the stimulus. The intensity of the 460 nm channel was adjustable by the subject through a neutral density, compensated wedge whose setting could be recorded by a push-button. The flicker frequency was also under the subject's control via a potentiometer. An adjustable dental impression bite ensured accurate and steady positioning of the subject's eye relative to the exit pupil.

The flicker frequency was set to a pre-determined value which, for central viewing by the subject, would allow flicker to be eliminated only over a very small range of wedge settings. This frequency was in the 25 to 35 Hz range. Having set the wedge to meet the no-flicker condition, the subject adapted to the viewing conditions by fixating with one eye on the stimulus cross-hairs for two minutes. The subject's other eye was occluded by an eye-patch. At the end of this period, the subject proceeded to make a series of 10 to 15 wedge settings, attempting to obtain the center of the no-flicker range. The wedge was randomly offset after each setting. On occasions, the subject could not eliminate flicker entirely but instead sought a condition of minimum flicker. This was followed by another series of 10 to 15 settings while fixating on the LED, the frequency having been reduced to 12 to 16 Hz in order to reduce the range of no-flicker. The whole procedure was then repeated for the subject's other eye. The optical density of the macular pigment of the subject was measured daily for a period of one week prior to the commencement of lutein supplementation and daily thereafter.

Figure 4A:
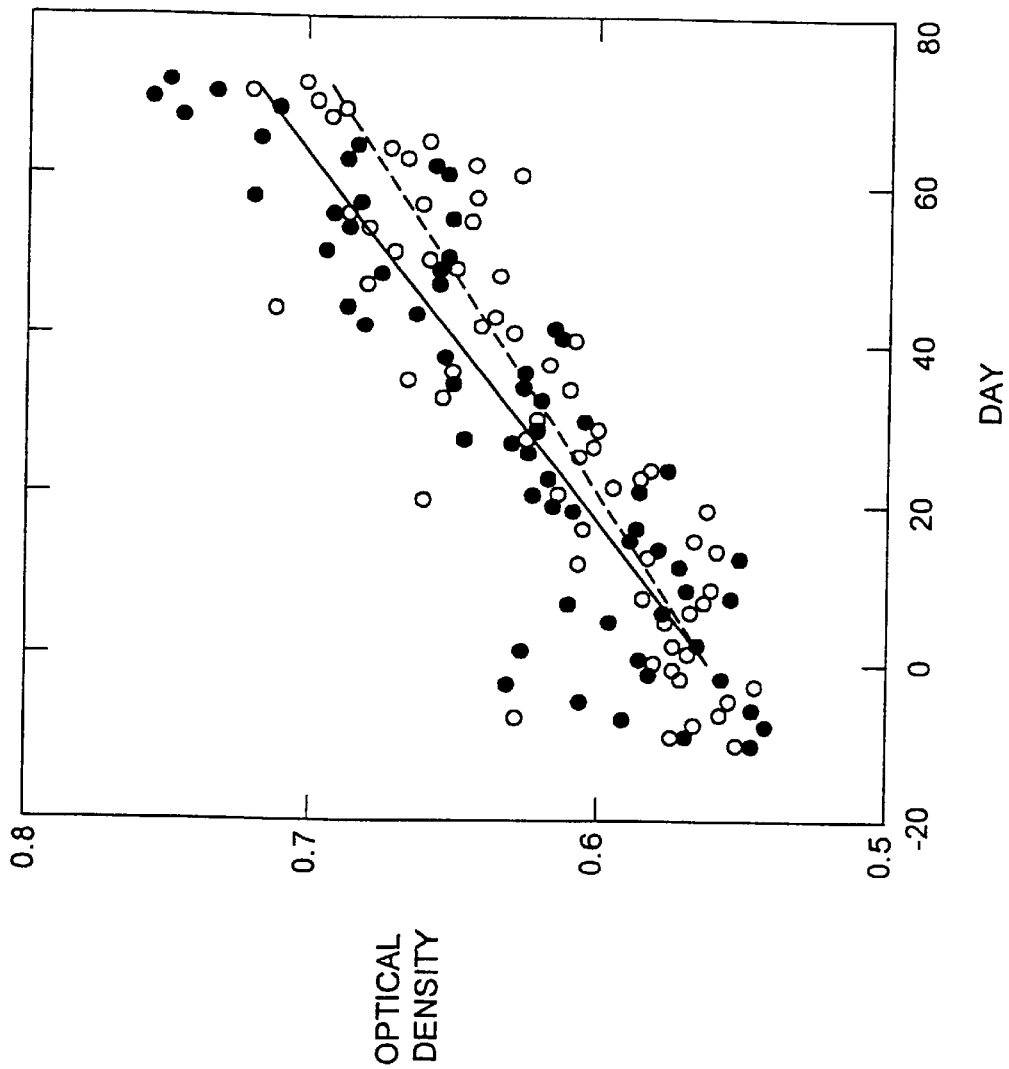
FIG. 4a shows the daily macular pigment optical density measurements for subject JTL (Example 2) from 7 days prior to the start day (day "0") of the lutein supplementation through day 72. Left eye—solid circles; right eye—open circles. The solid line is the linear least squares fit to the left eye data and has a slope of $15.3 \times 10^{-3}$ absorbance units per week.
Figure 4B:
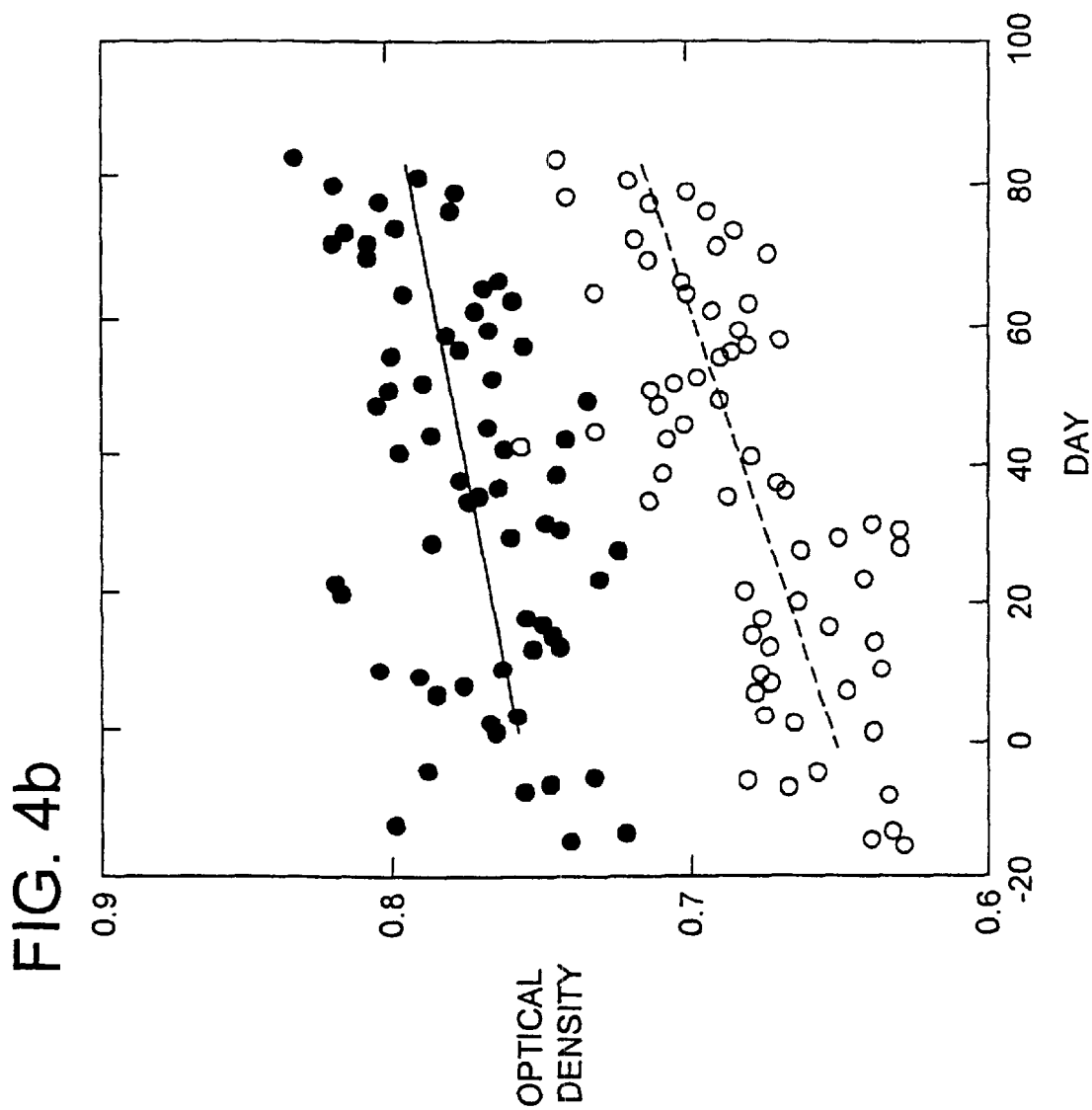
FIG. 4b shows the daily macular pigment optical density measurements for subject RAB (Example 2) from 7 days prior to the start day (day "0") of the lutein supplementation through day 83. Left eye—solid circles; right eye—open circles. The solid line is the linear least squares fit to the left eye data and has a slope of $3.1-10^{-3}$ absorbance units per week. the dashed line is a fit to the right eye data and has a slope of $2.3 \times 10^{-3}$ absorbance units per week.
Figure 5A:
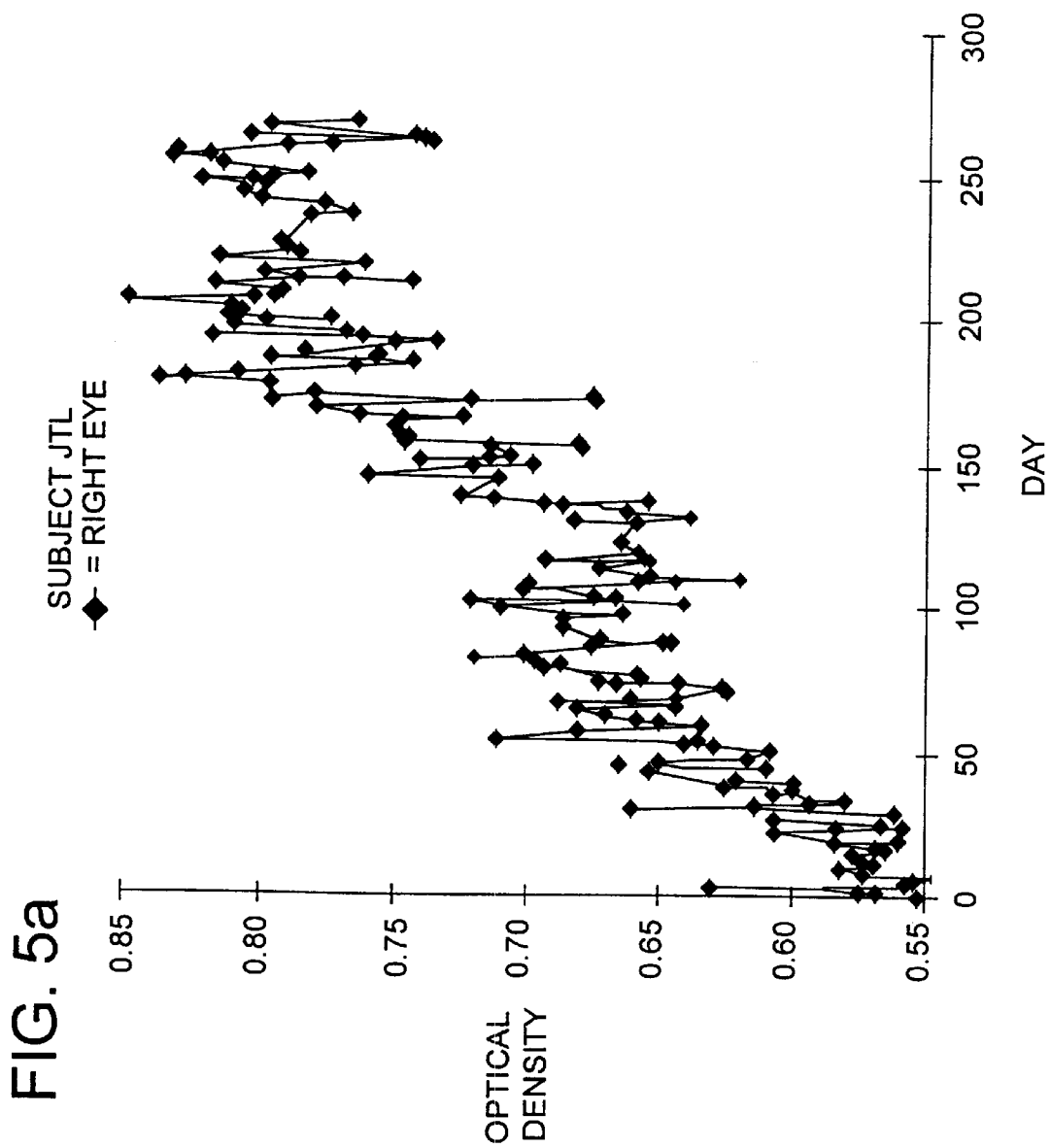
FIGS. 5a, 5b and 5c show the daily macular pigment optical density measurements for the same subject as is the case in FIG. 4a for a longer period of lutein administration which includes the period represented in FIG. 4a, FIG. 5a relating to the right eye of the subject, FIG. 5b relating to the left eye and FIG. 5c representing the L-R average.
Figure 5B:
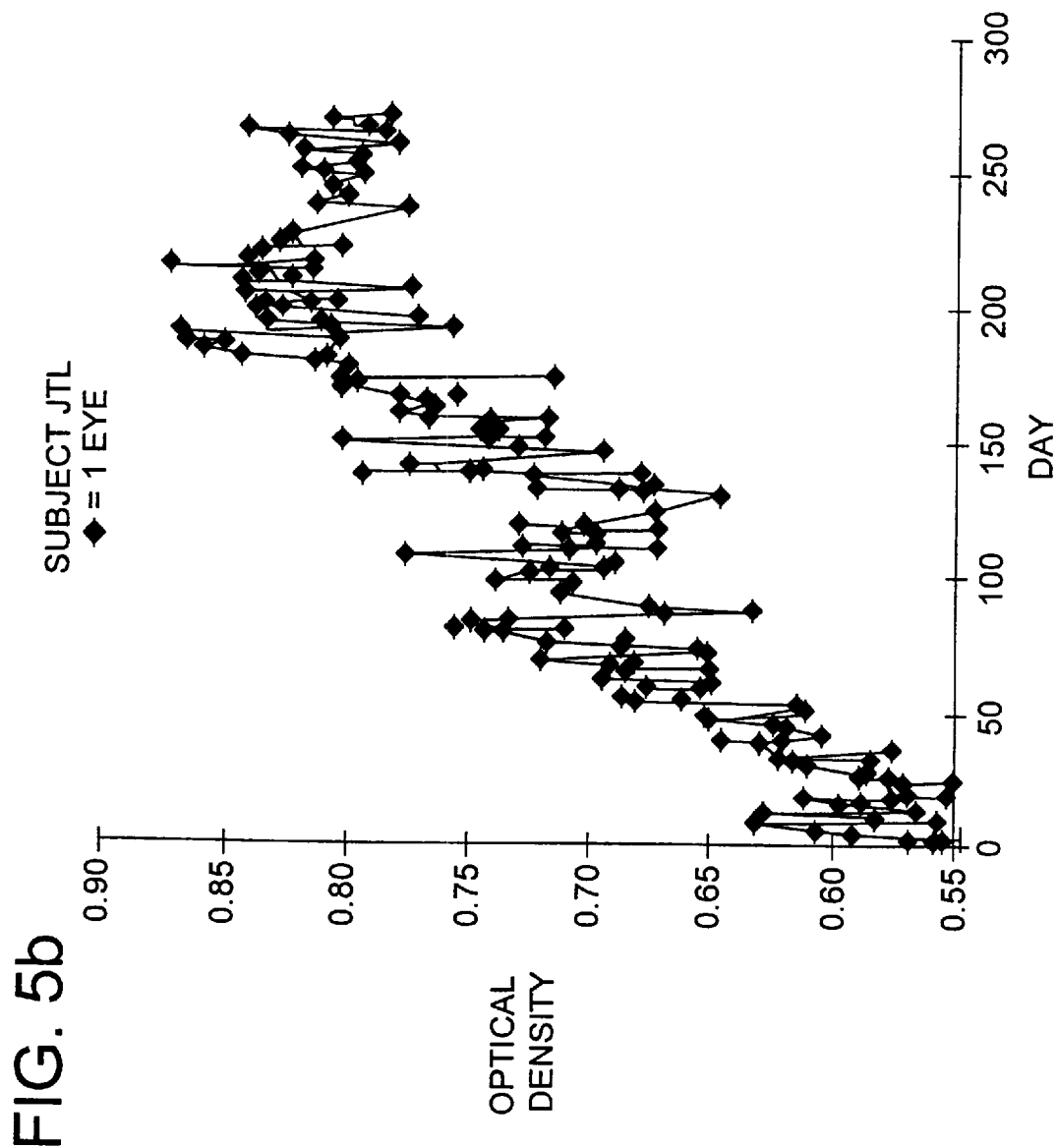
Figure 5C:
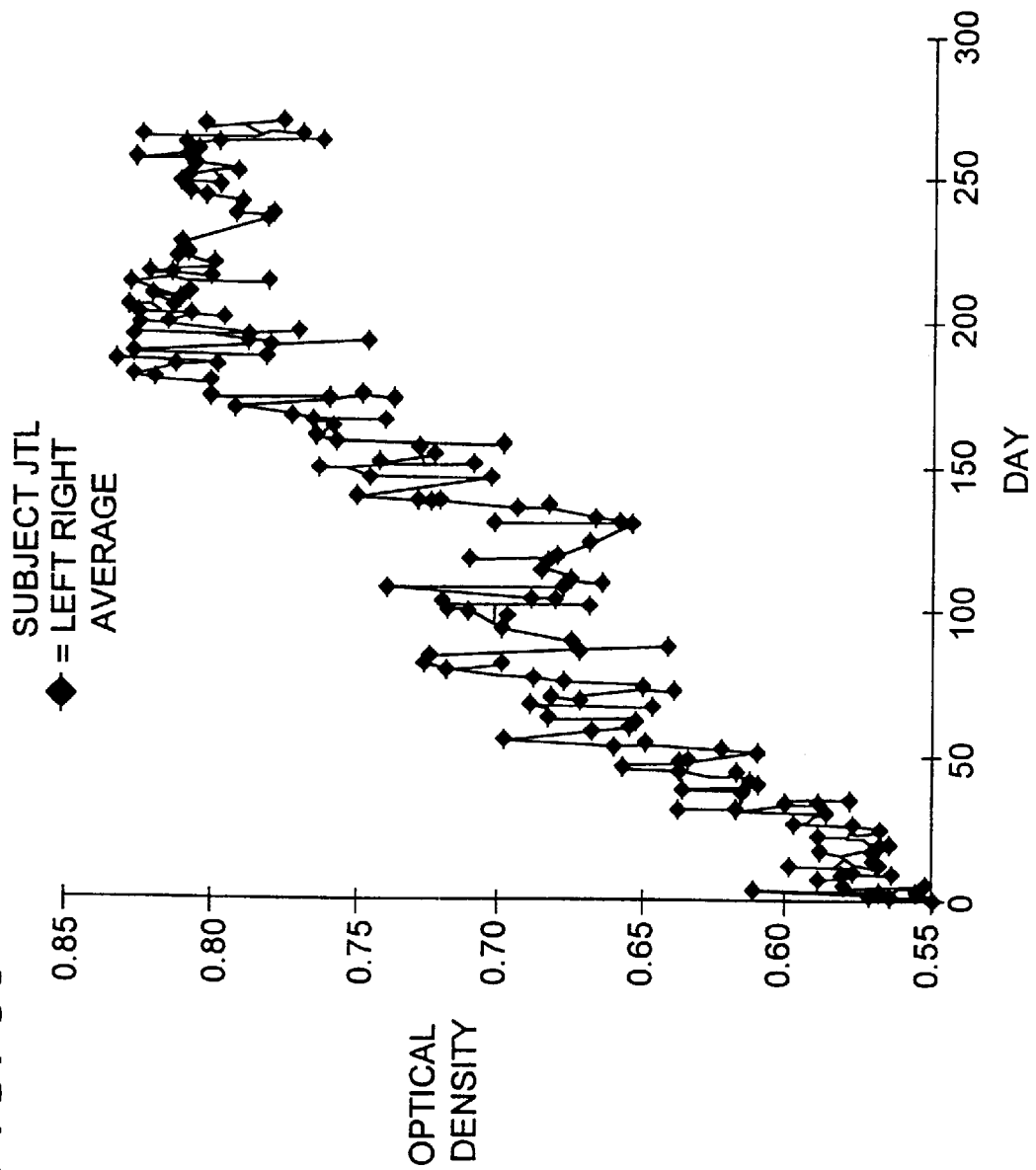

FIGS. 4a and 4b show the absorbancy of the macular pigment during the time course of the experiments in the two subjects. An increase in the macular pigment level of subject JTL was first observable on the 14th day of supplementation. This subject had macular pigment levels in both eyes that were experimentally determined by repeated measurements to be equal (±2%) the initial values of 0.57 and 0.58 being determined by averaging 15 measurements obtained over a 17 day time period. Comparison of these values with the average of 15 measurements obtained over the 18 day period at the end of the experiment gave values of 0.67 and 0.70 for the right and left eye, respectively, showing that the increase in optical density of the macular pigment is highly significant $p<0.0005$ for both the right and left eye, based on a one sided t test. After discontinuing the dose of lutein at day 138, optical density continued to rise until about day 180 and then reached a plateau.

For subject RAB, right and left eyes were found to have significantly different macular pigment density. The initial mean value for the right eye was 0.66 while that of the left eye was 0.76. This corresponded to a difference of 15% between the subject's left and right eyes. The increase in macular pigment determined by comparing the initial averages for each eye and the final average (0.70 right, 0.79 left) was found to be highly significant ($p<0.001$).

After discontinuing the dose at day 138, the optical density continued to rise in both eyes until day 200 and then reached a plateau. After several weeks of administration of lutein, the palms of the hands of each subject turned a noticeable yellow colour. This condition is similar to that induced by beta-carotene at the same dose.

Two other subjects LLM and KES receiving 30 mg/day lutein ester were examined. For subject LLM after 75 days the macular pigment had increased in both eyes from 0.3 to 0.5 optical density and then reached a plateau.

For subject KES, the data had a much larger spread of values and an increase was only apparent in the left eye of optical density from 0.3 to 0.5.

Macular pigmentation increase was shown to be a slow process, despite the high plasma lutein levels. This may be partly due to the need for lutein to diffuse into the avascular macular region of the retina. One would expect meso-zeaxanthin to be as active or more active than lutein.

The trial established a relationship between the increased serum levels of lutein and corresponding increases in the concentration of lutein in the macula of the human eye. Long term lutein supplement of individuals having low levels of macular pigmentation could result in a significant increase in the level of pigmentation within the macula.

Our data suggests that macular pigmentation does function to protect the retina. An increased rate of photo oxidation might accompany lower macular pigment levels in some individuals and could contribute to a more rapid build up of pathological lesions associated with AMD.

EXAMPLE 3

A capsule was prepared using the following ingredients by simple admixture and routine encapsulations:

| Ingredients per capsule | Mg per Capsule |
| --- | --- |
| Meso-zeaxanthin | 10 |
| Lecithin | 50 |
| Soya Bean oil | 200 |

One capsule per day/after a meal is recommended.

EXAMPLE 4

A capsule was prepared using the following ingredients by simple admixture and routine encapsulation:

| Ingredients per capsule | mg per Capsule |
| --- | --- |
| Lutein Ester | 75 (equivalent to 10 mg lutein) |
| Meso-zeaxanthin | 75 |
| Lecithin | 25 |
| Soya Bean Oil | 100 |

The above is a mixture of 50% each carotenoid. In the above capsule, lutein could be replaced by R, R' zeaxanthin).

EXAMPLE 5

A capsule was prepared using the following ingredients by simple admixture and routine encapsulation:

| Ingredients per capsule | mg per Capsule |
|---|---|
| Vitamin C (ascorbic Acid) | 160 |
| α-tocopheral | 110 |
| Meso-zeaxanthin | 90 |
| Lecithin | 25 |
| Soya Bean oil | 75 |

A suitable daily dose for treatment AMD would be one-two capsules daily.

EXAMPLE 6

The procedure of Example 7 was repeated except that 30 mg of Coenzyme Q10 was included in the mixture.

EXAMPLE 7

A size 12 oval capsule of nominally 800 mg weight was prepared from the following ingredients by simple admixture and routine encapsulation:

TABLE 2

| Ingredients per capsule | mg per Capsule |
|---|---|
| Vitamin A Palmitate 1500 iu/gm | 1.277 |
| Carotene Oil | 52.5 |
| Meso-zeaxanthin | 7.5 |
| Vitamin C (Ascorbic Acid) | 105 |
| Mixed Tocopherols 1000 iu/gm | 149 |
| Selenium Yeast 1000 mcg/gm | 90 |
| Copper Gluconate to give | 22.26 |
| Zinc Gluconate to give | 117 |
| Manganese Gluconate to give | 36.4 |
| Vegetable Shortening | 56 |
| Beeswax | 23 |
| Lecithin | 22 |
| Soya Bean Oil | 75.563 |
| | 800 |

One capsule per day is very suitable for long term administration and has in addition valuable antioxidant properties.

EXAMPLE 8

A dry powder formula diet composition was prepared by mixing 5–10 mg of meso-zeaxanthin with a Cambridge Diet (The Cambridge Diet is a Registered Trade Mark) product obtained from Cambridge Health Plan Ltd., Norwich, England under the product identification.

EXAMPLE 10

Measurement of meso-zeaxanthin in human retinas

Retinas were first cut be circular punches into an inner disc (inner annulus) of 3 mm diameter which encompassed most of the macular retina, a medial reing (medial annulus) encompassing the retinal tissues between 3 and 11 mm in diameter, and an outer ring (outer annulus) encompassing the retinal tissues between 11 and 22 mm in diameter.

Table 3 contains data derived from these retinal analyses. From these data it can be concluded that individuals suffering from this disease had much less lutein and zeaxanthin in their retinas than individuals not suffering from this disease. In most cases, the medial and outer annuli lie outside the macular area, and, as such, would not generally be affected by this disease. For AMD eyes, the reduced concentrations of lutein and zeaxanthin in areas outside the macula (medial and outer annuli) are clear evidence that these eyes suffered from a deficiency in these compounds and that the reductions measured were not simply a sequellae of the disease itself. The concentrations of both lutein and total zeaxanthin are reduced in the eyes of individuals reportedly suffering from age-related macular degeneration.

TABLE 3

Analysis of Human Retinas from AMD and non-AMD (Control) Eyes
Concentrations in picomoles of compound per square millimeter of retina

| Compound: | Control Eyes Annulus | | | AMD Eyes Annulus | | | Loss/Gain in AMD Eyes (%) Annulus | | |
|---|---|---|---|---|---|---|---|---|---|
| Total Zeaxanthin | 3.451 | 0.130 | 0.027 | 2.055 | 0.097 | 0.022 | −40% | −25% | −19% |
| Total Lutein | 2.313 | 0.187 | 0.058 | 1.462 | 0.127 | 0.045 | −37% | −32% | −22% |

When the total zeaxanthin in the retina was further analyzed, the data demonstrated that retinal zeaxanthin is a mixture of the three isomeric forms (3R,3'R-zeaxanthin, 3R,3'S-(meso)-zeaxanthin and 3S,3'S-zeaxanthin). The concentration of 3S,3'S-zeaxanthin is barely detectable in any annulus, and is, therefore, negligible for the purposes of this Declaration. However, the concentration of meso-zeaxanthin is substantial.

Table 4 summarizes the results of comparative analyses between non-ARMD (Control) retinas and retinas afflicted with age-related macular degeneration.

TABLE 4

Analysis of Zeaxanthin in Human Retina from AMD and non-AMD (Control) Eyes.
Concentrations in picomoles zeaxanthin per square millimeter of retina

| Isomer: | Control Eyes Annulus | | | AMD Eyes Annulus | | | Loss/Gain in AMD Eyes (%) Annulus | | |
|---|---|---|---|---|---|---|---|---|---|
| | Inner | Medial | Outer | Inner | Medial | Outer | Inner | Medial | Outer |
| R,R'-Zeaxanthin | 1.730 | 0.094 | 0.02 | 1.399 | 0.087 | 0.025 | −19% | −7% | +25% |
| Meso-Zeaxanthin | 1.399 | 0.037 | 0.006 | 0.993 | 0.032 | 0.005 | −30% | −14% | −17% |

As can be seen from the data, meso-zeaxanthin is reduced by 30% in the inner annulus of AMD eyes, by 14% in the medial annulus and by 17% in the outer annulus. FIGS. 6–8 show this data in graphic format for the Inner, Medial and Outer Annuli, respectively. The data in Table 4 and in FIG. 8 demonstrate that the concentration of R,R-zeaxanthin in the outer annulus is actually greater in AMD eyes than in Control eyes. This is both counter-intuitive and totally unexpected in light of other data for the same set of eyes (e.g. concentrations of lutein and total zeaxanthin). In addition, the mean concentrations of meso-zeaxanthin in these annuli are 17% lower in AMD eyes than in the Controls. In fact, the loss of meso-zeaxanthin in AMD eyes is greater than the loss of R,R'-zeaxanthin across all annuli. It is evident from these data that meso-zeaxanthin contributes significantly to the differences measured in total zeaxanthin given in Table 3, while the natural form of zeaxanthin (R,R') does not. The surprising and unexpected selective reduction in meso-zeaxanthin in the macula of AMD eyes would not have been predicted from dietary and blood studies. The results suggest that treatment of AMD by administration of meso-zeaxanthin should require much lower dosages than would be necessary for the other carotenoid compounds such as lutein. It is expected that amounts as low as 0.5 mg per day could be effective in the prevention or treatment of AMD. Dosages between 0.5 and 50 mg/day, preferably 1–20 mg/day, most preferably 5–15 mg/day are expected to be effective.

Publications cited herein are hereby incorporated by reference and are listed below for convenience.

References

Bone, R. A. and Landrum, J. T. (1984). Macular pigment in Henle fiber membranes: a model for Haidinger's brushes. Vision Res. 24, 103–108.

Bone, R. A. and Landrum, J. T., and Cains, A. (1992). Optical density of the macular pigment in vivo and in vitro Vision Res. 32, 105–110.

Bone, R. A. and Landrum, J. T., Hime, G. W., Cains, A. and Zamor, J. (1993). Stereochemistry of the human macular carotenoids. Invest. Opthalmol. Vis. Sci., 34, 2033–2040.

Bone, R. A. and Landrum, J. T., and Tarsis, S. I. (1985). Preliminary identification of the human macular pigment. Vision Res. 25, 1531–1535.

Bone, R. A. and Sparrock, J. M. B. (1971). Comparison of macular pigment densities in human eyes. Vision Res. 11, 1057–1064.

Davson, H. (1990). "Physiology of the Eye". Pergamon Press, Inc., New York.

Ditchbum, R. W. (1973). "Eye-Movements and Visual Perception". Clarendon Press, Oxford.

Eye Disease Case—Control Study Group (1893). Antioxidant status and neovascular age-related macular degeneration. Arch. Ophthalmol. 111, 104–109.

Feeney-Burns, L., and Ellersieck, M. R. (1985). Age-related changes in the ultrastructure of Bruch's membrane. Am.J.Ophthalmol. 100, 886–697.

Gottsch, J. D., Pou, S., Bynoa, L. A., and Rosen, G. M. (1990). Hematogenous photosensitization. A mechanism for development of age-related macular degeneration. Invest. Opthalmol. Vis. Sci. 31, 1674–1692.

Guiliano, A. R., Matzner, M. B., and Canfield, L. M. (1993). Assessing variability in quantitation of carotenoids in human plasma: variance component model. In "Methods in Enzymology" (L. Packer, ed.), Vol. 214, pp. 94–101. Academic Press, San Diego.

Guth, S. L., Massof, R. W., and Benzschawel, T. (1980), Vector model for normal and dichromatic colour vision. J.Opt.Soc. Am. 70, 197–212.

Hammond, B. R., Jr., Fuld, K., and Curran-Celentano, J. (1995a). Macular pigment density in monozygotic twins. Invest. Ophthalmol. Vis. Sci. 36, 2531–3541.

Handelmann, G. J., Shen, B., and Krinsky, N. I. (1992). High resolution analysis of carotenoids in human plasma by high-performance liquid chromatography. In "Methods in Enzymology" (L. Packer, ed.), Vol. 213, pp. 336–346. Academic Press, San Diego.

Kirshfeld, K. (1982). Carotenoid pigments: their possible role in protecting against photooxidation in eyes and photoreceptor cells. Proc. R. Soc. Lond. B216, 71–85.

Landrum, J. T., Bone, R. A., Vidal, I., Menendez, E. and Kilburn, M. (1995). Macular pigment stereomers in individual eyes: a comparison between normals and those with age-related macular degeneration. Adv. Pharmacol. 113, 1518–1523.

Mares-Periman, J. A., Brady, W. E., Klein, R., Klein, B. E. K., Palta, M., Bowen, P., and Stacewicz-Sapuntzakis, M. (1994). Serumn levels of carotenoids and tocopherols in people with age-related maculopathy. Invest. Ophthalmol. Vis. Sci. 35, (suppl.) 3455.

Pease, P. L., Adam, A. J., and Nuccio, E. (1987). Optical density of human macular pigment. Vision Res., 27, 705–710.

Reading, V. M., and Weale, R. A. (1974). Macular pigment and chromatic aberration. J. Opt. Soc. Am. 64, 231–234.

Ruttimann, A., Schiedt, T., and Vecci, M. (1983). Separation of (3R,3'R)-, (3R,3'S;meso)-(3S,3'S)-zeaxanthin, (3R,3'R, 6'R)-(3R,3'S,6'S)-, and (3S,3'S,6'S)-lutein via the dicarbamates of(S)-(−)-1-[1-naphthyl]ethylisocyanate. J. High. Res. Chrom. Commun. 6, 612–616.

Scheidt, K., Bischof, S., and Glinz, E. (1995). Example 5: Fish-isolation of astaxanthin and its metabolites from skin of Atlantic Salmon (Salmo salor). In "Carotenoids" (G. Britton, S. Liaaen-Jenson, H. Pfander, eds.). pp. 243–252. Birkhauser Verlag, Basel.

Seddan, J. M., Umed, A. et al. (1994). Dietary Cartoneoids, Vitamins A. C, and E, and Advanced Age-Related Macular Degeneration. J.A.M.A, 272, 1413–1420.

Wald, C. (1945). "Human vision and the spectrum". Nature (London). 101, 653–658.

Walls, G. L. (1967). "The Vertebrate Eye and its Adaptive Radiation", Hafner, N.Y.

Werner, J. S., Donnelly, S. K., and Kliegl, R. (1987). Ageing and human macular pigment density. Appended with translations from the work of Max Schutze and Ewald Horing. Vision Res. 27, 257–268.

Wooten, B. R., and Wald, G. (1973). Colorvision mechanism in the peripheral retinas of normal and dichromatic observers. J. Gen. Physiol. 61, 125–145.

Wysecki, G., and Stiles, W. S. (1982). "Quantitative Data and Formulae". Wiley, N.Y.

What is claimed is:

1. A pharmaceutical composition comprising an effective dose of meso-zeaxanthin and a carrier or diluent.

2. The composition of claim 1 wherein the amount is at least 0.5 mg.

3. The composition of claim 1 wherein the amount is no more than 50 mg.

4. The composition of claim 1 wherein the amount is less than 7.5 mg.

5. The composition of claim 1 wherein the amount is between 5 and 15 mg.

6. The composition of claim 1, further comprising another biologically active constituent.

7. The composition of claim 6, wherein the other biologically active constituent is an anti-oxidant.

8. The composition of claim 7, wherein said anti-oxidant is another carotenoid, or is vitamin A, vitamin C, vitamin E, selenium, copper, zinc, manganese or ubiquinone.

9. The composition of claim 8, wherein said other caroteoid is lutein, an isomer of zeaxanthin other than mesozeaxanthin; lycopene; or alpha, beta, gamma or delta carotene.

10. The composition of claim 1 that also contains at least one compound selected from the group consisting of lutein, 3R, 3'R zeaxanthin and 3S,3'S zeaxanthin.

11. A method of producing a pharmaceutical composition containing meso-zeaxanthin, said method comprising mixing meso-zeaxanthin with a pharmaceutically acceptable carrier or diluent.

* * * * *